United States Patent
Espina Perez et al.

(10) Patent No.: US 8,310,938 B2
(45) Date of Patent: Nov. 13, 2012

(54) DETECTING AND DISCRIMINATING BETWEEN INTERFERENCE CAUSED BY DIFFERENT WIRELESS TECHNOLOGIES

(75) Inventors: Javier Espina Perez, Aachen (DE); Daniel Martinez Gamote, Madrid (ES)

(73) Assignee: Koninklijke Philips Electronics N.V., Eindhoven (NL)

(*) Notice: Subject to any disclaimer, the term of this patent is extended or adjusted under 35 U.S.C. 154(b) by 478 days.

(21) Appl. No.: 12/531,697

(22) PCT Filed: Mar. 31, 2008

(86) PCT No.: PCT/IB2008/051203
§ 371 (c)(1),
(2), (4) Date: Sep. 17, 2009

(87) PCT Pub. No.: WO2008/122916
PCT Pub. Date: Oct. 16, 2008

(65) Prior Publication Data
US 2010/0097951 A1  Apr. 22, 2010

(30) Foreign Application Priority Data
Apr. 4, 2007  (EP) .................................. 07105629

(51) Int. Cl.
H04J 3/14 (2006.01)
(52) U.S. Cl. ........................ 370/241; 370/310
(58) Field of Classification Search .................. None
See application file for complete search history.

(56) References Cited

U.S. PATENT DOCUMENTS

| | | |
|---|---|---|
| 2002/0080855 A1 | 6/2002 | Watanabe et al. |
| 2002/0122462 A1 | 9/2002 | Batra et al. |
| 2003/0058829 A1 | 3/2003 | Batra |
| 2003/0198200 A1 | 10/2003 | Diener et al. |
| 2003/0198304 A1 | 10/2003 | Sugar et al. |
| 2004/0156440 A1 | 8/2004 | Sugar et al. |
| 2005/0220135 A1 | 10/2005 | Honda et al. |
| 2006/0014536 A1 | 1/2006 | Demirhan et al. |
| 2006/0056492 A1 | 3/2006 | Honda |
| 2006/0089103 A1 | 4/2006 | Osburn |
| 2010/0041358 A1* | 2/2010 | Wood ......................... 455/226.3 |

FOREIGN PATENT DOCUMENTS

| | | |
|---|---|---|
| GB | 2422968 A | 8/2006 |
| WO | 2005099293 A1 | 10/2005 |

* cited by examiner

*Primary Examiner* — Kevin C Harper

(57) ABSTRACT

There is provided a method and a device for detecting interfering radio technologies. The method in accordance with the invention is applicable in order to detect and identify possible interfering technologies that can be found, e.g., in the 2.4 GHz ISM band, by use of a device having a single transceiver which is adapted to employ a first wireless radio access technology. For example, a device having an IEEE 102.15.4 cordless transceiver is able to identify according to the method in accordance with the invention radio signals sent by disquieters which use other interfering technologies by use of only this transceiver. The device can for example be a sensor of a wireless body sensor network.

17 Claims, 11 Drawing Sheets

| Technology | Bandwidth | Number of channels | Frequency gap between channels | Frequency hopping | Slotted? | Range |
|---|---|---|---|---|---|---|
| IEEE 802.15.4 | 2 MHz | 16 | 3 MHz | NO | NO | approx. 5-10m |
| Bluetooth | 1 MHz | 23 (JP, ES, FR) or 79 | 0 MHz | YES | YES | approx. 1-10m |
| WiFi | 22 MHz | 11 (USA, CA) or 13 (EU) | overlapping | NO | NO | approx. 10-100m |
| Microwaves | Variable | - | - | NO | - | - |

FIG. 3

IEEE 802.11b/g frequency channels [19]

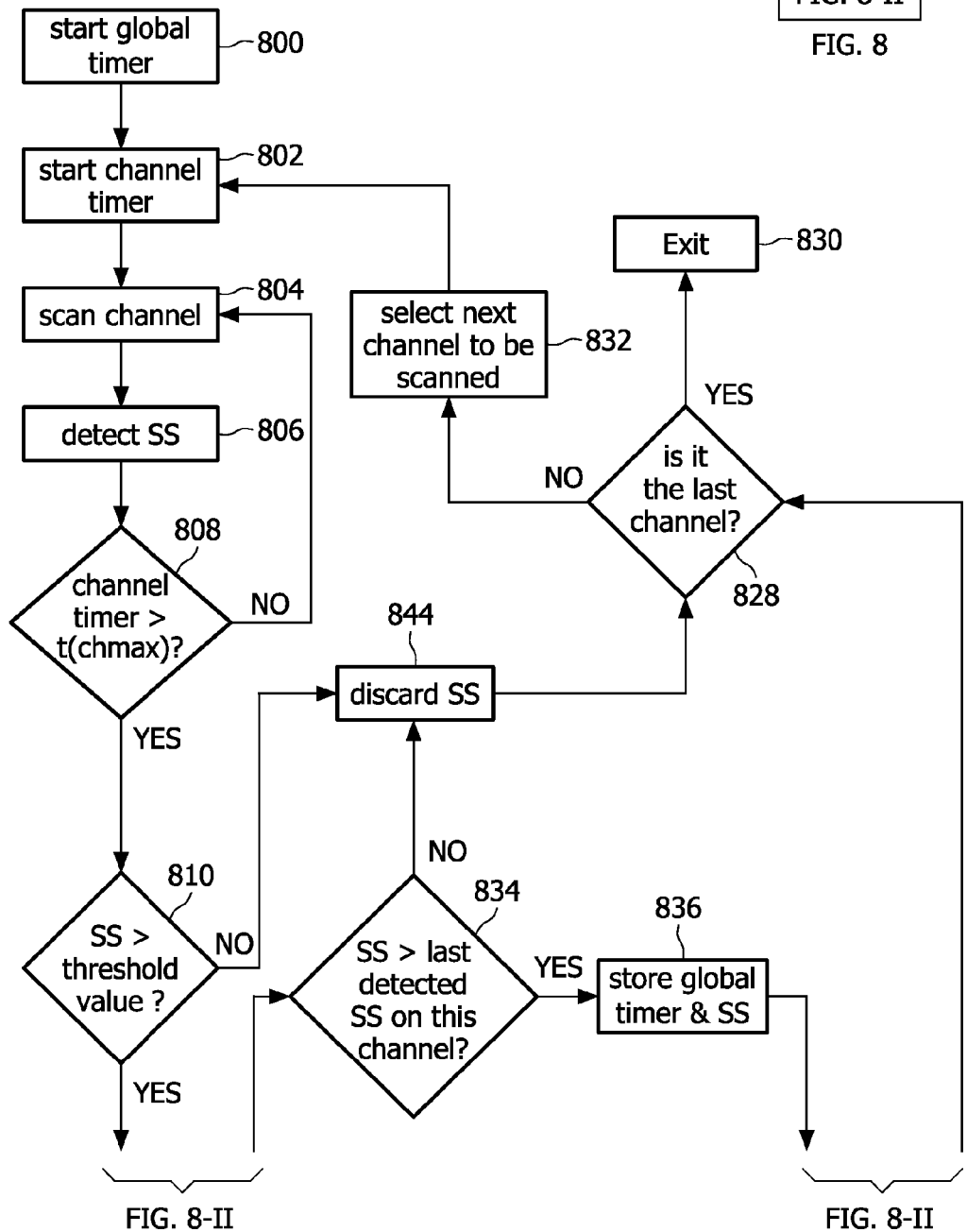
FIG. 8-I

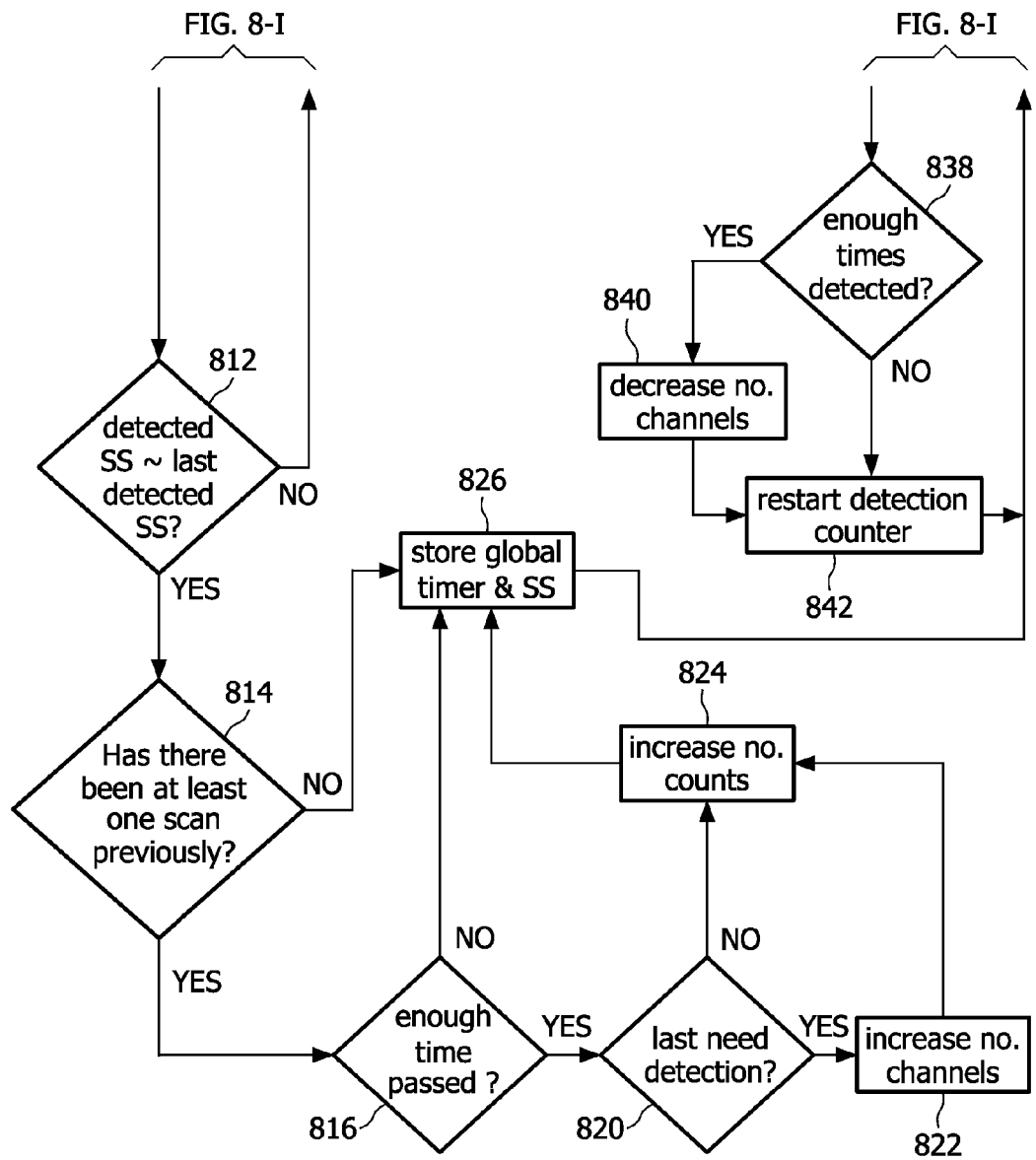
FIG. 8-II

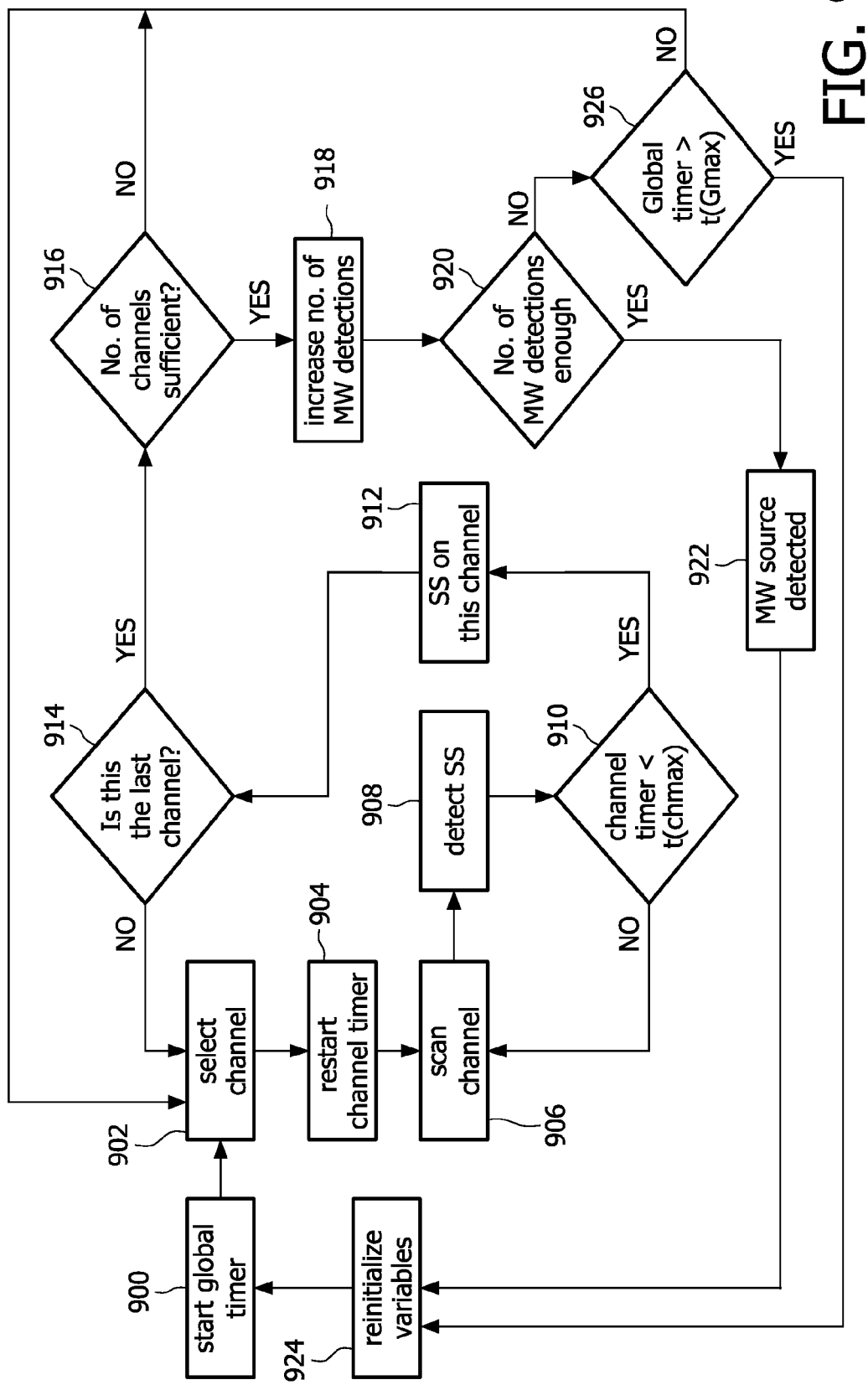

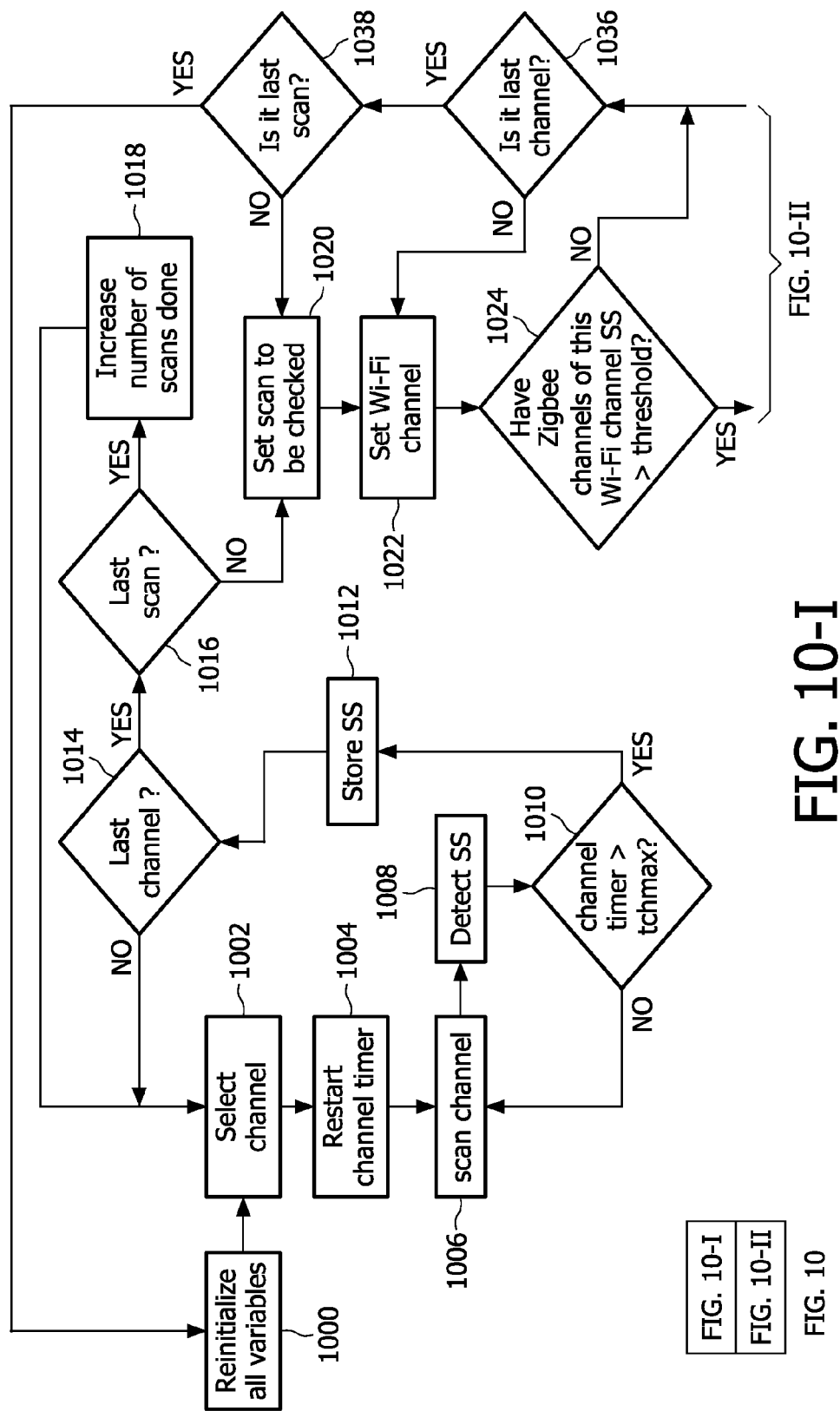
FIG. 10-I

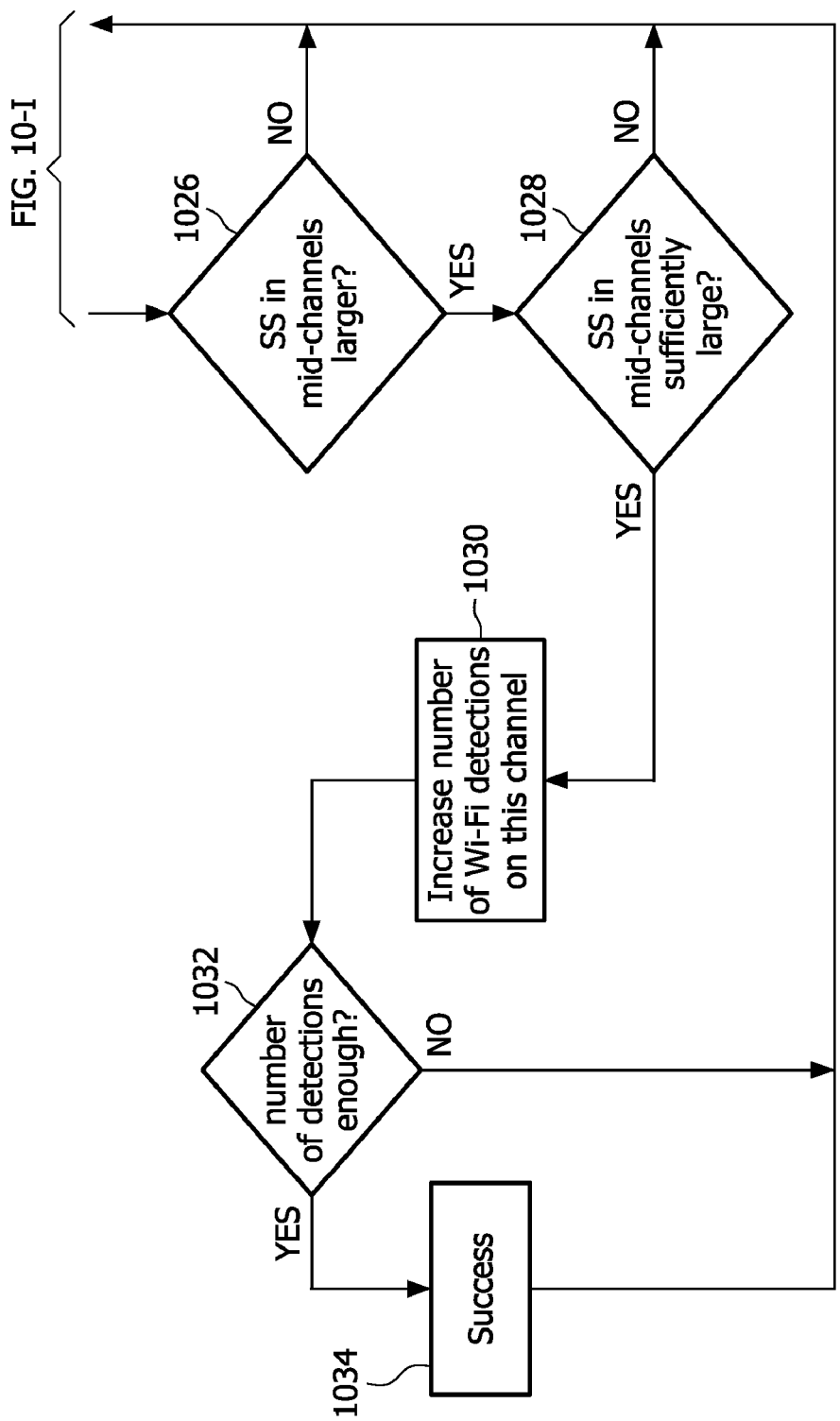
FIG. 10-II

US 8,310,938 B2

DETECTING AND DISCRIMINATING BETWEEN INTERFERENCE CAUSED BY DIFFERENT WIRELESS TECHNOLOGIES

FIELD OF THE INVENTION

The invention relates to a method of detecting interfering technologies. The invention also relates to a computer program product which has instructions that are adapted to perform the method in accordance with the invention, and to a device. The invention also relates to a body sensor and to a body sensor network.

BACKGROUND AND RELATED ART

Monitoring of vital signs is essential for patients in intensive care units, for patients suffering from chronic illnesses, and in post-operation situations. For this purpose, sensors are commonly attached to a patient's body that are usually connected to a bedside monitor which shows the state of the received vital parameters. Nowadays, the sensors and the monitor are connected by wires. This reduces the patient's mobility and makes the work of nursing staff more difficult, for example, because all the wired connections between the sensors and the monitor must be set up.

In order to increase the patient's mobility, to make the work of nursing staff easier and to get a flexible sensor system in aspects as quantity of sensors, diversity of applications, etc., the concept of body sensor networks (BSN) has been developed. In body sensor networks, the communication between the sensors attached to a patient or between a sensor and the monitor is based on wireless communication links. In order to ensure interoperability on the one hand in between the sensors and on the other hand between the sensors and the monitor, an open standard is typically used as communication protocol. Open standards that are for example employed are: the IEEE 802.15.1 standard which is also known as Bluetooth, the WiFi standard (IEEE 802.11), and the Zigbee standard (IEEE 802.15.4).

As the applications that the sensors of a body sensor network will carry out are critical, the communication between the monitor and the sensors must be reliable at least in a short range around the patient in order to ensure correct monitoring. Other wireless networks or other devices employing a wireless communication technology might however generate interfering radio signals that might disturb the communication between the sensors of the body sensor network or between a sensor and the bedside monitor of the body sensor network. A body sensor network might for example employ the Zigbee standard for communication. The frequency band employed by the Zigbee standard lies within the ISM radio band around 2.4 GHz. A device, e.g. a laptop, in close vicinity to the body sensor network might for example employ the Bluetooth standard. The device therefore generates radio signals that interfere with the radio signals in accordance with the Zigbee standard and might cause a malfunction of the communication in the body sensor network.

Another interfering technology might be due to a microwave oven which emits radio waves with frequencies in the ISM band.

As the applications that the sensors carry out are critical, the communication between the monitor and the sensors must be reliable at least in the short range around the patient to ensure a correct monitoring. As a consequence, interfering technologies should be detected by the body sensor network or, more precisely, by one or more of the sensors or by the monitor of the body sensor network in order to ensure a proper operation of the network. The term interfering technology is within this document used in order to refer to a source which generates radio signals that might interfere with the radio signals used for wireless communication in between a wireless body sensor network and that might therefore disturb the communication in the wireless body sensor network.

The document US 2006/0089103 A1 discloses a radio frequency source detector which is built with the purpose of detecting and analysing RF (radio frequency) signals in order to determine the source of interference. The source detector is useful for installing and troubleshooting a wireless local area network (WLAN) or similar communication devices. The detector includes a receiver to receive RF signals from unknown RF sources, a processor for determining the level and characteristics of the RF signals and for determining the identities of unknown RF sources, and a display on which the processor displays the identities of the RF sources.

It is an object of the invention to provide an improved device for detecting interfering sources of radio signals and to identify the underlying technology. It is a further object of the invention to provide an improved method of detecting interfering sources of radio signals and identifying the underlying technology.

SUMMARY OF THE INVENTION

According to a first aspect of the invention, there is provided a method for detecting interfering technologies. In accordance with an embodiment of the invention, the method is performed by a device which comprises a transceiver. The transceiver is adapted to employ a first wireless radio access technology. The method in accordance with the invention comprises the scanning a first plurality of frequency channels provided by the first wireless radio access technology for radio signals of a first interfering technology. The first plurality of frequency channels relates to frequency channels provided by the first wireless radio access technology in which radio signals of the first interfering technology being expected. Further, the presence of a radio signal in a frequency channel of the first plurality of frequency channels is detected by measuring a first signal strength of the radio signal. The first interfering technology is identified as source of the detected radio signals, if in a preset number of frequency channels of the first plurality of frequency channels a radio signal is detected via the corresponding first signal strength. Otherwise a second plurality of frequency channels provided by the first wireless radio access technology are scanned for radio signals of a second interfering technology, if the preset number of frequency channels will not be reached during the scanning for the first interfering technology.

The device therefore employs a first wireless radio access technology for communication with other devices. In particular, the device is a sensor or a component of a sensor of a body sensor network and employs the first wireless radio access technology, e.g., Zigbee, for communication within the network. After having chosen the first wireless radio access technology, interfering technologies can be identified. For example, the parameters of the radio signals emitted in accordance with the Zigbee standard are known, e.g. from the standard's specifications. The same is true for all other open standards. Thus, the other open standards can be analysed and the ones that employ radio signals that overlap in frequency with the radio signals employed by Zigbee can be identified. The transceiver which is adapted to employ, e.g. the Zigbee standard, is then used to detect the other interfering technologies known to employ radio signals with frequencies that overlap with the frequencies employed by Zigbee.

Furthermore, radio signals emitted by microwave ovens can be detected by use of the transceiver. Microwave signals emitted by a microwave oven are not standardized as is the case with the radio signals employed by the open standards. However, if the characteristics of microwave signals are known, for example from experimental results, an expected signal pattern for the frequency channels employed by the first wireless radio access technology can be specified from the experimental results.

The term interfering technology is therefore used in the scope of this document in order to refer to the open standards communication technologies and in order to refer to microwaves emitted by microwave ovens. The other devices using the interfering technologies in the vicinity of device in accordance with the invention can be regarded as disquieters.

It can therefore be determined in advance that in the first plurality of frequency channels radio signals are to be expected when a disquieter in the vicinity of the device employs the first interfering technology. The frequency channels of the first plurality of frequency channels are then scanned for the radio signals, that are determined via the detection of the corresponding signal strengths. The first interfering technology is then identified as source of the detected radio signals, if the following criteria is fulfilled: In a preset number of frequency channels scanned, a radio signal must be detected. If it becomes clear during the scanning process that the preset number of frequency channels will not be reachable, it is not further scanned any more for the first interfering technology.

Instead, it is scanned for the second interfering technology in the second plurality of frequency channels. The first and second plurality of frequency channels might completely, partly or not at all overlap. In case there is an overlap, the signal strengths measured so far when scanning for the first interference technology are further used for the identification of the second interfering technology. Moreover, the signal strength or the detected pattern of the signal strength, e.g., the distribution of the detected signal strengths in the frequency channels is employed for deciding for which interfering technology is scanned next.

Interfering technologies can relatively easily be detected by use of the corresponding transceiver. In principle the device could be equipped with a plurality of transceivers, wherein each transceiver is adapted to employ the interfering technology which shall be detected by the transceiver. Sensors of a body sensor network should however be kept as small and as light as possible in order to allow a high mobility of the patient and not to disturb the patient. Many transceivers in the device thus increase the size, weight and power consumption of the device. As however the device employing the method in accordance with the invention only uses the one transceiver which is anyways used for communication also for the detection of a plurality of interfering technologies, the weight, size, and power consumption will not increase due to the provision of the possibility to identify interfering technologies.

In accordance with an embodiment of the invention, at least the first signal strength and a second signal strength are measured in each frequency channel, wherein the second signal strength is measured for the radio signal detected subsequently to the radio signal having the first signal strength. The method in accordance with the invention further comprises the step of determining a first time period relating to the time elapsed between the detection of the first signal strength and the detection of the second signal strength. In a further step, the first time period is compared with a given second time period specified for the first interfering technology, wherein the first interfering technology is identified as source of the radio signals, if for the preset number of frequency channels, the first time period determined for a frequency channel of the preset number of frequency channels at least approximately matches the second time period specified for the frequency channel.

The first interfering technology might relate to an interfering technology, e.g., Bluetooth, which employs frequency hopping. Bluetooth emits pulses of radio signals that are also referred to as bursts of radio signals, whereby the frequencies of these signals change according to a distinctive algorithm within the frequency channels employed by Bluetooth. Hence, a first burst having a frequency that falls within the frequency of a frequency channel of the first plurality of frequency channels provided by the first wireless radio access technology will be detected due to a measurement of the corresponding first signal strength of the first burst in this channel. A second burst, or more precisely the second signal strength of the second burst will be measured a given time span later in this channel. The given time span is characteristic for Bluetooth and can therefore be used among other criteria to identify a disquieter employing Bluetooth. The method in accordance with the invention is particularly advantageous as it allows to identify interfering technologies which employ a frequency hopping scheme.

In accordance with an embodiment of the invention, the method further comprises the step of determining for each frequency channel of the first plurality of frequency channels a number of detections, wherein the number of detections relates to the number of times a radio signal is detected in the corresponding frequency channel. In a further step, the number of frequency channels in the first plurality of frequency channels for which the number of detections exceeds an expected number of detections is determined, wherein the expected number of detections is specified for the first interfering technologies. The number of frequency channels for which the expected number of detections exceeds the expected number of detections provides an indication for the presence of at least a second interfering technology.

It might well be that there are two or more interfering technologies present. The first interfering technology scanned for is employing a frequency hopping scheme. The first plurality of frequency channels in which it is scanned for the first interfering technology can only relate to the frequency channels provided by the first wireless radio access technology in which a radio signal of the first interfering technology is expected. Due to the frequency hopping employed by the first interfering technology, the number of detections (the number of times a radio signal above the threshold value is detected in a channel) will be similar in all channels of the plurality of channels. Hence, if there are some channels in the plurality of channels which have a significantly higher number of detections than the count rate, then this is an indication for the presence of at least a second interfering technology. The method in accordance with the invention is therefore particularly advantageous as parallel to the detection of the first interfering technology which employs a frequency hopping algorithm an indication of the presence of at least a second interfering technology which does not employ a frequency hopping algorithm can be detected.

In accordance with an embodiment of the invention, the first plurality of frequency channels is scanned sequentially. Furthermore, the first plurality of frequency channels is scanned at most for the duration of the given time window, and each frequency channel of the first plurality of frequency channels is scanned at most for the duration of a frequency channel scanning time window. The scanning time used for identifying the first interfering technology is compared with the minimum required scanning time, wherein the minimum required scanning time is specified for the first interfering technology. The first interfering technology is identified as not being the source of the radio signals, if the scanning time spent to detect the first interfering technology is below the minimum required scanning time.

In accordance with an embodiment of the invention, the first plurality of frequency channels in which it is scanned for radio signals is selected according to characteristics of the first interfering technology. As mentioned above, not all frequency channels provided by the first wireless radio access technology are scanned for radio signals. Instead, only the frequency channels in which a radio signal emitted by a device employing the first interfering technology are scanned. This is particularly advantageous in order to improve the total scanning time for identifying the presence of a disquieter employing the first interfering technology and, as already laid out above, in order to identify the presence of at least a second interfering technology which does not employ a frequency hopping algorithm if it is scanned for the first interfering technology which employs the frequency hopping algorithm.

In accordance with an embodiment of the invention, the first plurality of frequency channels is scanned sequentially, wherein each frequency channel of the first plurality of frequency channels is scanned until a preset number of radio signals are detected. The scanning time for detecting the preset number of radio signals is compared with a minimum required scanning time which is specified for the first interfering technology. The first interfering technology is identified as not being the source of the radio signals detected in the channel, if the actual scanning time is below the minimum required scanning time. Otherwise, another interfering technology such as the second interfering technology is taken into account as source of the detected radio signals.

In accordance with an embodiment of the invention, a first spectrum shape specifies for the first plurality of frequency channels expected relative signal strengths for the first interfering technology, wherein the at least first signal strengths measured in frequency channels of the first plurality of frequency are employed to determine relative first signal strengths for the frequency channels, wherein the first interfering technology is identified as source of the detected radio signals, if the relative first signal strengths determined for the frequency channels in which the at least first signals strength have been detected match the expected relative expected relative signal strengths specified for the frequency channels.

The first spectrum shape therefore specifies for each frequency channel an expected relative signal strength. The relative signal strengths can for example be scaled with respect to the signal strength of a particular channel. For example, Zigbee provides 16 Channels, whereby the $11^{th}$ channel at a frequency of 2405 MHz and the $12^{th}$ channel at a frequency of 2410 MHz overlap with a WLAN-channel, whereas the WLAN signal in the frequency range of the $11^{th}$ channel is about half as strong as the WLAN signal in the frequency range of the $12^{th}$ channel. The first spectrum shape might relate to the WLAN standard and might therefore specify that in the $12^{th}$ Zigbee channel a relative signal strength of 1 is to be expected when a disquieter employs the WLAN channel that falls within this channel. Further, with respect to Channel 11, the spectrum mask specifies that a signal strength of 0.5 is to be expected with respect to the $12^{th}$ Channel.

In accordance with the invention, the first signal strength is measured in a first frequency channel of the first plurality of frequency channels, wherein a third signal strength is measured in a second frequency channel of the first plurality of frequency channels, wherein a first ratio is determined between the first signal strength and the third signal strength, wherein a second ratio is determined between the expected signal strengths specified by the first spectrum shape for the first and second frequency channels, wherein the first and the second ratio are compared, wherein the first interfering technology is not considered as source if the first ratio does not at least approximately match the second ratio. The presence of the first interference technology could therefore be excluded quickly simply by checking if the first ratio derived from measured signal strengths in the first and second channels matches the second ratio.

In accordance with an embodiment of the invention, a second spectrum shape is specified for the second interfering technology, wherein a third ratio is determined between the expected signal strengths specified by the second spectrum shape for the first and second frequency channels, wherein it is further scanned for the second interfering technology if the first ratio does at least approximately match the third ratio.

In accordance with an embodiment of the invention, the method further comprises the step of measuring a pulse length for each detected radio signal, wherein the pulse length of a radio signal relates to the period of time during which the signal strength of the radio signal is above a preset threshold value. In a further step, the measured pulse lengths of the detected radio signals are compared with an expected pulse length for the first interfering technology, wherein the first interfering technology is identified as source of some of the detected radio signals, if at least some of the measured pulse lengths match the expected pulse length.

In accordance with an embodiment of the invention, the measured pulse lengths which do not match the expected pulse length specified for the first interfering technology are compared with expected pulse lengths specified for other interfering technologies. One of the other interfering technologies, e.g., the second interfering technology, is then identified as a source of some of the detected radio signals, if at least some of the measured pulse length match the expected pulse length specified for the corresponding other interfering technology.

According to a second aspect of the invention, there is provided a computer program product comprising computer executable instructions which are adapted to perform the method in accordance with the invention.

According to a third aspect of the invention, there is provided a device. In accordance with an embodiment of the invention, the device is a sensor. In accordance with another embodiment of the invention, the device is a component of a sensor or of a patient monitor of a body sensor network.

According to a fourth aspect of the invention, there is provided the body sensor network comprising one or more devices in accordance with the invention.

The method in accordance with the invention is applicable in order to detect and identify possible interfering technologies that can be found, e.g., in the 2.4 GHz ISM band, by use of a single transceiver which is adapted to employ a first wireless radio access technology. For example, a device having an IEEE 102.15.4 cordless transceiver is able to identify according to the method in accordance with the invention radio signals sent by disquieters which use other interfering technologies by use of only this transceiver. The use of a single transceiver to detect various interfering technologies provides the advantage that the device can be built relatively compact and light. The device can therefore be employed as sensor in a body sensor network or be implemented in a sensor of a body sensor network which is further adapted to monitor vital signals of a patient.

These and other aspects of the invention will be apparent from and elucidated with reference to the embodiments described hereinafter.

BRIEF DESCRIPTION OF THE DRAWINGS

In the following embodiments of the invention will be described in greater detail by making reference to the drawings in which:

FIG. 3 shows a table giving parameters of several technologies generating signals in the ISM band, FIG. 8 shows another flow diagram illustrating steps performed by a method in accordance with the invention, FIG. 9 shows another flow diagram illustrating steps performed by a method in accordance with the invention, FIG. 10 shows another flow diagram illustrating steps performed by a method in accordance with the invention.

DETAILED DESCRIPTION

Figure 1:
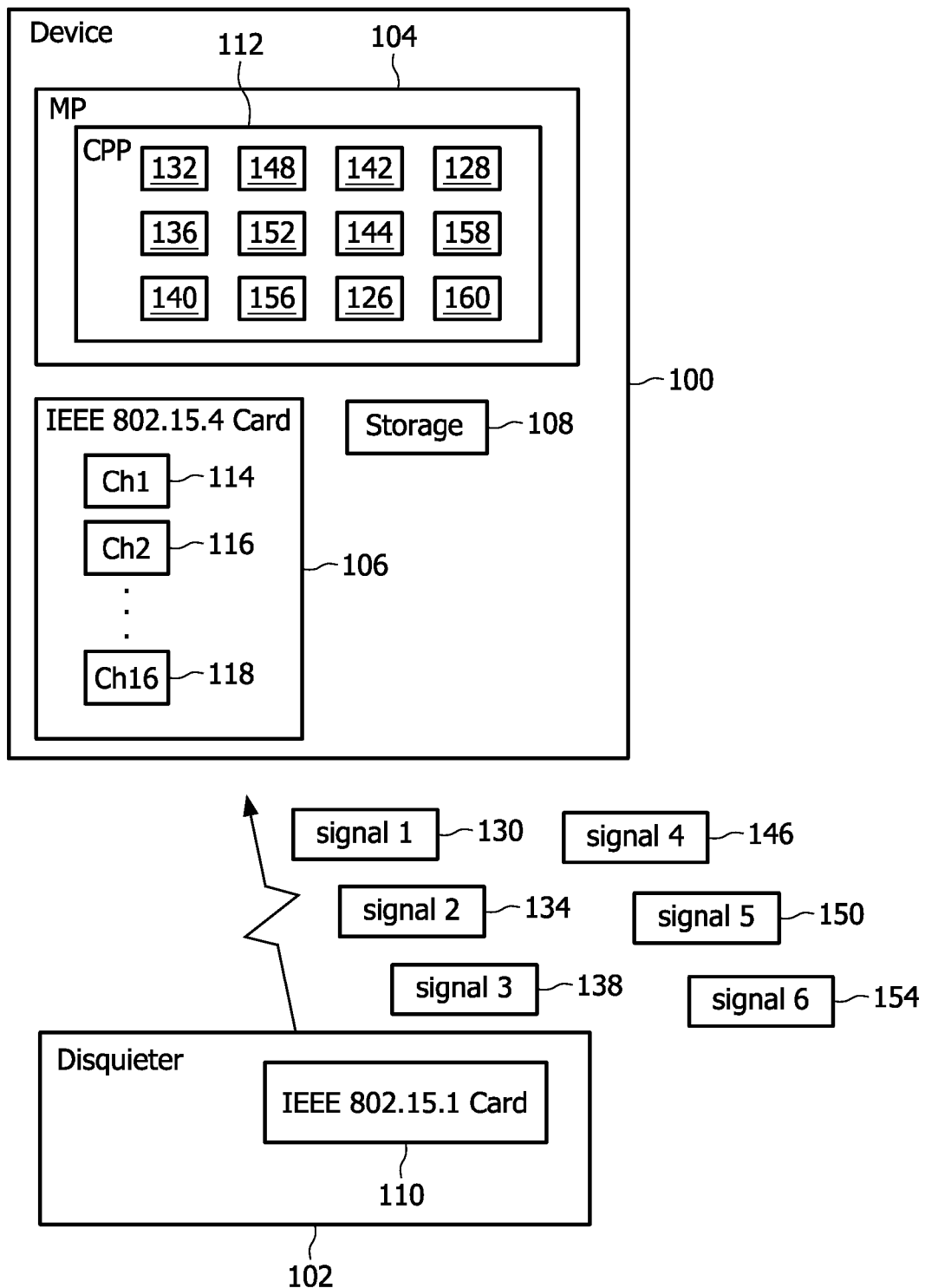
FIG. 1 shows schematically a block diagram of a device and a disquieter in accordance with the invention.

FIG. 1 shows schematically a block diagram of a device 100 in accordance with the invention and of a disquieter 102. The disquieter 102 might be a source of disturbance to the device 100. The device 100 comprises a microprocessor 104, an IEEE 802.15.4 card 106, and a storage 108. The microprocessor 104 executes a computer program product 112 which is permanently stored on the storage 108 and loaded for execution into the microprocessor 104.

The IEEE 802.15.4 card 106 can be used to communicate with other devices not shown in FIG. 1 via the Zigbee protocol. The device 100 can therefore be a component of a wireless network such as a body sensor network in which the Zigbee standard is employed for communication in between the nodes of the network. The IEEE 108.15.4 card 106 is adapted to employ 16 channels in accordance with the IEEE 802.15.4 standard which lie in the 2.4. GHz frequency band. For example, a frequency channel 1 114 (the frequency channel with the lowest frequency) lies at a frequency of 2405 MHz, the neighbouring frequency channel 2 116 lies at a frequency of 2410 MHz, and the frequency channel 16 118 (the channel with the highest frequency) lies at 2480 MHz (the cited frequencies relate to the centre frequencies of the frequency channels).

The disquieter 102 is able to use the Bluetooth standard as the disquieter 102 is equipped with an IEEE 802.15.1 card 110. The Bluetooth standard specifies 23 or 79 channels depending on the country in which it is used and that lie also within the 2.4 GHz frequency. Some frequency channels employed by the Bluetooth card 110 overlap with the frequency channels of the Zigbee card 106. In fact, each Zigbee frequency channel overlaps with a Bluetooth channel. Hence, interfering radio signals can be sent by this Bluetooth channels that might disturb the communication of the Zigbee channels.

In order to detect the presence of the disquieter 102 which employs the Bluetooth standard for communication, the microprocessor 104 executes the computer program product 112. The computer program product 112 is employed for detecting interfering technologies such as for example Bluetooth. For this, the characteristics of Bluetooth which are known for example from the standard or which have been determined by measurements previously undertaken, are implemented within the computer program product 112.

In order to scan for Bluetooth signals, the channels 114-118 are therefore scanned consecutively for the duration of a given time window 126. Each channel is further scanned for a given frequency channel scanning time window 128. The computer program product 112 therefore initiates the scanning of the channel 1 114 for the frequency channel scanning time window 128. After the frequency channel scanning time window 128 has been passed, the frequency channel 2 116 is scanned and so on until the scanning of the channel 16 118 has been finished. If the duration as specified by the given time window 126 has not yet been reached, the scanning process is repeated with channel 1 114, and so on.

While channel 1 114 is scanned, the disquieter 102 might emit a signal 130. Signal 130 is detected while scanning the frequency channel 1 114, if the frequency of the signal 130 overlaps with the channel frequency. If this is the case, the first signal strength 132 is detected for the signal 130. The first signal strength 132 can be compared with a threshold 142 which is specified for this interfering technology. If the signal strength 132 is below the threshold 142, the detected value is discarded. Otherwise it is stored on the storage 108.

Similarly, a signal strength 136 can be detected for a signal 134, if it is emitted by the disquieter 102 and if the signal 134 is at a frequency that falls within the frequency span of channel 116. The signal strength 136 is also compared with the expected threshold 142 and, if it is larger than the threshold 142, it is stored on storage 108 and otherwise discarded.

Furthermore, while scanning channel 16 118, signal strength 140 of a signal 138 emitted by the disquieter 102 can be detected. The signal strength 140 is also stored on the storage 108 if it is larger than the threshold value 142 and discarded otherwise.

As mentioned above, the detection of a Bluetooth signal is expected for each Zigbee frequency channel. Thus, the detection of a signal on each Zigbee frequency channel could be used to determine the interfering technology to be based on Bluetooth. However, microwaves emitted by microwave ovens, have frequencies that cover the full range of the Zigbee channels. Hence, the criteria mentioned above is not yet sufficient to distinguish Bluetooth signals from microwaves emitted by a microwave oven.

Bluetooth employs however a frequency hoping scheme. A Bluetooth radio signal detected on a frequency channel provided by the Zigbee standard might therefore be followed by another Bluetooth signal after a given period of time. Thus, in frequency channel 114, a radio signal 146 is detected having a signal strength 148 a first period of time 160 after the detection of the signal 130. Similarly, in frequency channel 116, a radio signal 150 having a signal strength 152 is detected the first period of time 160 after the detection of the signal 134. Moreover, in frequency channel 118, a radio signal 154 having a signal strength 156 is detected the first period of time 160 after the detection of the signal 138.

It is further determined during the scanning process if radio signals have been detected in a preset number 144 of frequency channels, and if the first period of time 160 measured in the radio channels matches a given period of time 158 which is specified for the Bluetooth standard. If the preset number 144 is reached, the scanning stops and the signals 130, 134, 138, 146, 150, 154 are identified as being related to the Bluetooth standard.

However, if it becomes clear that the preset number 144 of channels will not be reached, for example, if in too many channels no or not sufficient signal could be detected, the scanning process is restarted and it is scanned for another interfering technology. The signals so far detected could be employed as a basis for deciding for which of the other possible interfering shall be scanned. For example, if in a frequency channel, the pulses do not arrive regularly but completely irregularly, this cannot be due to a Bluetooth signal. Hence, this might be an indication for a microwave signal if in each Zigbee frequency channel such irregularities can be observed. Thus, if it is scanned for Bluetooth and (a) in each Zigbee channel signals are detected and (b) the signals arrive irregularly in all Zigbee channels, it might not be scanned until the end of the given time window 126 but the scan might be restarted and it might only be scanned for microwaves. Moreover, the so far measured signals might be employed to identify a microwave oven as being the source of the emitted signals.

Figure 2:
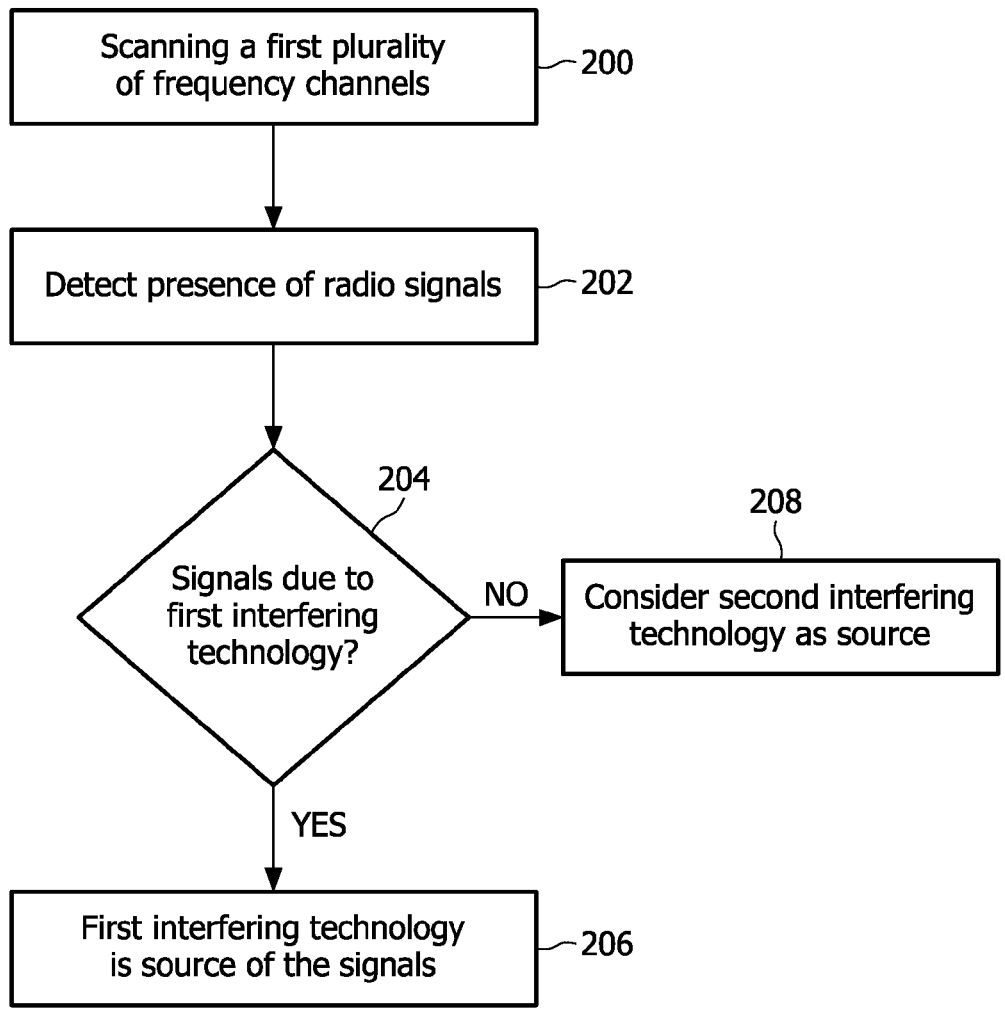
FIG. 2 shows a flow diagram illustrating steps performed by a method in accordance with the invention.

FIG. 2 shows a flow diagram illustrating steps performed by a method in accordance with the invention. The method in accordance with the invention is performed by a device which has a transceiver. The transceiver is adapted to employ a first wireless radio access technology. According to step 200 of the method, the device scans a first plurality of frequency channels provided by the first wireless radio access technology for radio signals of a first interfering technology, the first plurality of frequency channels relating to frequency channels provided by the first wireless radio access technology in which radio signals of the first interfering technology are expected. In step 202, the presence of a radio signal at a frequency which overlaps with the frequency of the frequency channel which is currently scanned is detected by measuring a first signal strength of the radio signal in this frequency channel. In step 204 it is determined if for a preset number of frequency channels of the first plurality of frequency channels the first signal strength of a radio signal is detected. If this is the case, the radio signals are identified in step 206 as being due to the first interfering technology. If this is not the case, the method proceeds with step 208, wherein a second plurality of frequency channels provided by the first wireless radio access technology is scanned for radio signals of a second interfering technology.

FIG. 3 shows a table which gives parameters of several technologies which employ or generate signals in the ISM-band. The IEEE 802.15.4 standard is also referred to as Zigbee and offers 16 channels, wherein each channel has a bandwidth of 2 MHz and wherein the gap between the channels is 3 MHz. Bluetooth is present on almost every cell phone, PDA and computer. This means that it can be easily found everywhere and it should be certainly considered as a source of disturbance to body sensor networks used in a hospital or at the patient's home. Its main characteristic as interference is that it is employing a frequency hopping scheme, whereby the average interference is actually divided by the number of channels Bluetooth has. Consequently it is not as harmful when interfering as it could be. Nevertheless, the counterpart is that the interference is unavoidable because changing the channel would not solve the problem.

WiFi is now commonly used on every laptop and it is even beginning to be used in cell phones, PDAs and other portable electronic devices and should therefore also be considered as the source of disturbance to body sensor networks employed in hospitals or at the patient's home. The WiFi channel covers 4 Zigbee channels at a time and therefore can be considered as a major source of disturbances to body sensor networks which employ the Zigbee standard for communication.

Microwaves are completely different with respect to the above mentioned technologies. Microwave ovens are however widely used, even in hospitals. However, while microwave ovens will roughly act as an interfering source in hospitals due to their usual distribution, microwaves can be hard interference when patient's monitoring is made at home, e.g., for chronic illness patients or elderly ones. Moreover microwave technology is a source of interference with particularly variable characteristics (power, type of microwave, meal being warmed, etc.).

The list of interfering technologies is however by no means restricted to the one given above. The list of interfering technologies can therefore be seen as an example of interfering technologies which can be detected via the method in accordance with the invention. In the following it is assumed that a device such as a body sensor in a body sensor network employs the Zigbee standard for communication within the network and tries to detect disquieters employing Bluetooth or WiFi, or which are microwave ovens.

Figure 4:
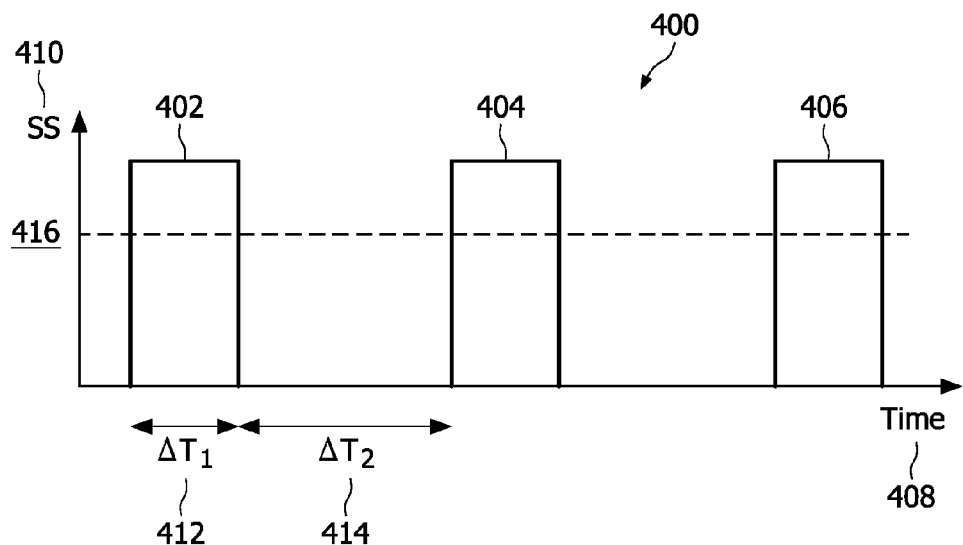
FIG. 4 shows a graph depicting the signal strengths of bursts detected in a frequency channel as a function of time.

FIG. 4 shows a graph 400 depicting signal strengths of bursts 402, 404, 406 as a function of time. The burst are also referred to as pulses. The abscissa 408 therefore corresponds to the time axis, whereas the ordinate 410 relates to the signal strength of the bursts 402-406 measured in a frequency channel of a Zigbee card. Bluetooth uses slotted transmissions with a basic time slot lasting 625 microseconds. Each packet can thereby last 1, 3 or 5 lots as the only possible transmission times. Moreover, Bluetooth employs frequency hopping. The period and the number of frequency channels used in the sequence depend on the task the Bluetooth device is doing. Depending on it, the sequences can be divided into two groups:

enquiry and paging sequences: 32 frequency channels equally distributed over the band, period length of 32, basic: 79 frequency channels (the whole band available to Bluetooth), very long period length, without repetitive patterns on short time periods but distributing the hopping sequence equally over all the channels during the short periods. This is the sequence used for transmissions.

The graph 400 shows the bursts 402, 404, and 406 that relate to Bluetooth packets and that have been detected in the Zigbee channel. Due to the fixed packet length, each burst detected has a period which relates to 1, 3 or 5 times the time slot length. Thus, the burst 402 has for example a duration of time 412 relating to 1 times the time slot length (625 microseconds). Moreover, due to the frequency hopping scheme, consecutive bursts will be detected in the channel after a specific time period 414.

Furthermore, the signal strengths of the Bluetooth bursts 402-406 will be above a threshold value 416 specified for the Bluetooth standard. Hence the time span 412, time period 414, as well as the threshold value 416 can be determined in advance and specified in the computer program product (cf. FIG. 1) in order to identify a disquieter employing the Bluetooth standard for communication via a Zigbee interface.

Figure 5:
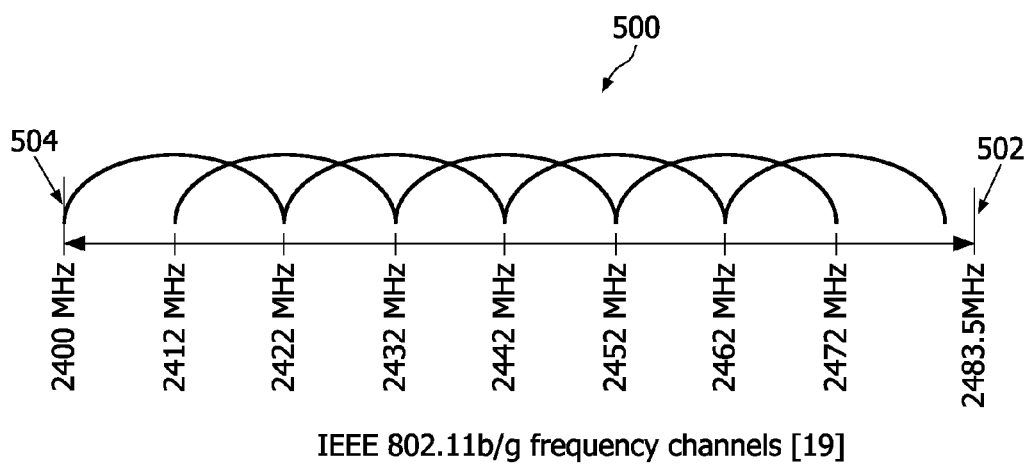
FIG. 5 shows schematically the distribution of the channels employed by IEEE 802.11 over the 2.4 GHz ISM band.

FIG. 5 shows schematically a graph 500 illustrating the distribution of some of the channels employable by IEEE 802.11 (WLAN) over the 2.4 GHz ISM band. The abscissa 502 of the graph 500 corresponds to a frequency axes, whereas the ordinate 504 depicts the magnitude of the signal strength.

As mentioned before, the Zigbee standard employs frequency channels that lie in the range from 2405 MHz and 2480 MHz. A disquieter employing one or more of the WLAN channels for communication will therefore cause disturbances on the Zigbee channels with which they overlap.

Figure 6:
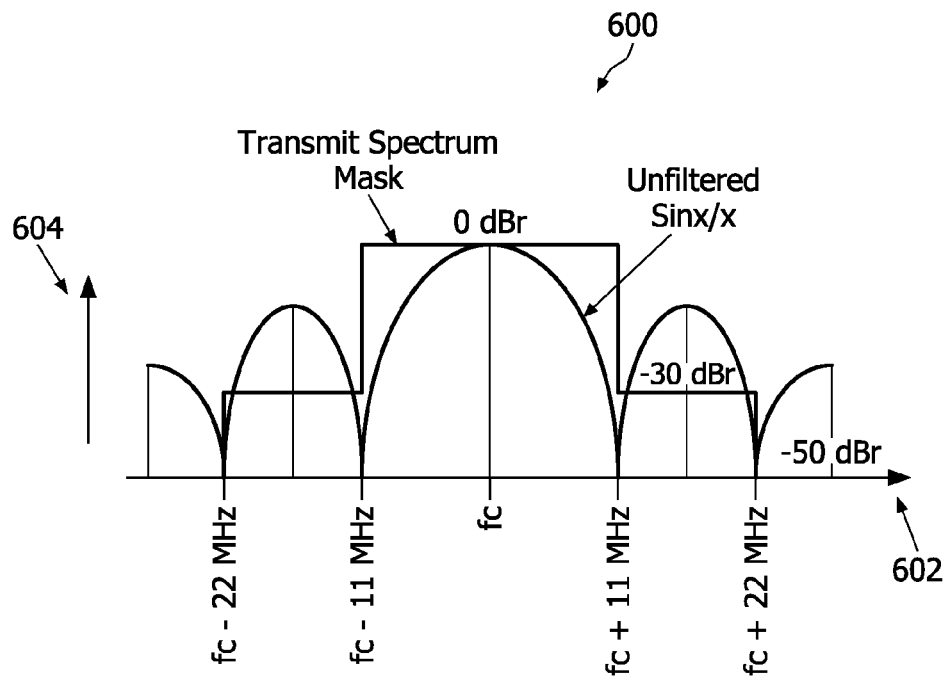
FIG. 6 shows schematically a spectrum of one of the channels employed by IEEE 802.11.

FIG. 6 shows schematically a spectrum 600 of one of the channels employed by IEEE 802.11. The abscissa 602 of the spectrum 600 corresponds to the frequency axis. The magnitude of the signal strength of the WLAN signal is depicted along the ordinate 604 of the spectrum 600. As can be seen, the spectrum 600 of a WLAN signal has a peak at a center frequency ($f_c$), minima with zero signal strength at $f_c \pm 11$ MHz and at $f_c \pm 22$ MHz, wherein a further peak is located between two minima which is smaller than the peak of the center frequency.

Figure 7:
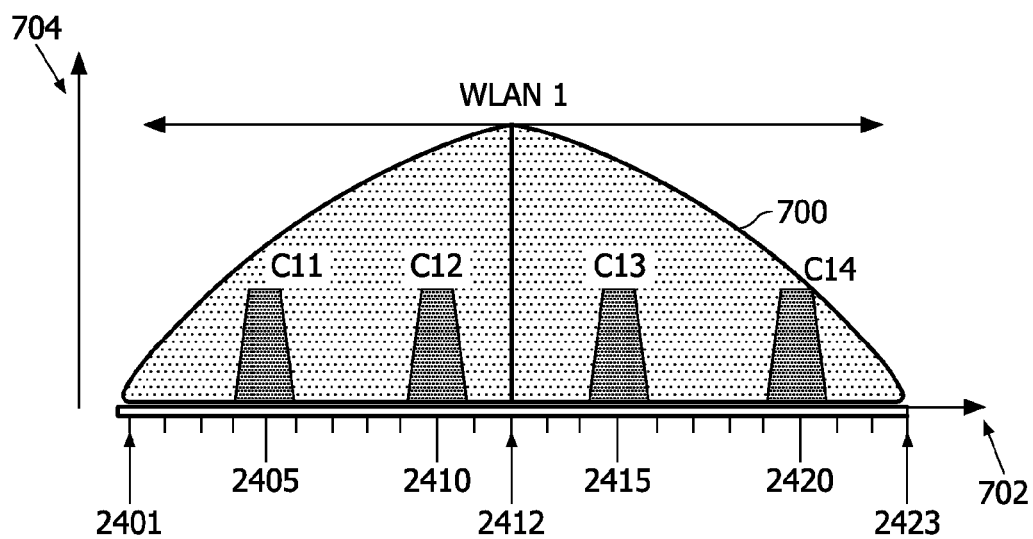
FIG. 7 illustrates the overlap between a frequency channel employed by IEEE 802.11 and frequency channels employed by IEEE 802.15.4.

FIG. 7 illustrates the overlap between a frequency channel 700 employed by IEEE 802.11 and 4 frequency channels (CH 11-CH 14) employed by IEEE 802.15.4 (Zigbee). The abscissa 702 relates to the frequency in MHz, whereas the ordinate 704 relates to the relative signal strength.

As shown in FIG. 6, a WLAN channel (IEEE 802.11) has a relative high signal strength at its center frequency, whereby the signal strength falls off with an increasing offset with respect to the center frequency (neglecting the minima). Such a WLAN signal can therefore be detected by use of the four neighbouring channels of the Zigbee standard (here the Channels CH 11 to CH 14).

In order to detect a WLAN channel by use of the Zigbee frequency channels, a first spectrum shape is specified, e.g., on the computer program which is according to an embodiment performing the method in accordance with the invention. The spectrum mask specifies for each frequency channel of the first plurality of frequency channels provided by the Zigbee standard an expected relative signal strength with the WLAN standard. According to FIG. 7, the spectrum mask specifies for CH 12, CH 13 of the Zigbee standard to expect a relative first signal strength, e.g. 1, and for the CH 11, CH 14 a second relative signal strength, e.g., 0.5, whereby the second signal strength is scaled to the first signal strength (The expected first signal strengths in CH 12 and CH 12 are about twice as strong as in CH 11 and CH 14).

The actual measured signal strengths in CH 11 and CH 14 are then scaled to the actual measured signal strengths measured in CH 12 and CH 13. If the actual signal strengths measured in CH 12 are about twice as strong as the actual measured signal strengths in CH 11 and CH 14 and if the actual signal strengths measured in CH 13 are also about twice as strong as the actual measured signal strengths in CH 11 and CH 14, then this provides a clear indication for the presence of a WLAN signal.

FIG. 8 shows another flow diagram illustrating steps performed by a method in accordance with the invention. The method in accordance with the invention is in particular applicable to detect a disquieter employing Bluetooth when the device employed for detection has a transceiver adapted for Zigbee. In step 800, a global timer is started after all other variables have been reinitialized. In step 802, a channel timer is started and a frequency channel of the plurality of channels is scanned in step 804. If during the scanning process a signal is detected, the signal strength is determined. If the actual signal strength is larger then a previously found signal strength, the actual signal strength is stored in step 806 while the previous one is discarded. In step 808, the actual scanning time monitored by the channel timer is checked against a preset maximal scanning time (tchmax). If the scanning time is smaller than the maximal scanning time, the method flows back to step 804. If the scanning time is larger than the maximal scanning time, the method proceeds with step 810.

In step 810, the stored signal strength is compared with a threshold value (specified for the Bluetooth standard). If the stored signal strength is larger than the threshold value, the method flows to step 812, where the stored signal strength is compared with the previously obtained ones. If the signal strength fits within the expected range, the detection continues with step 814. In step 814, it is checked, if there has already been at least one scan.

If this is the case, the method proceeds with step 816, where it is checked, if enough time has been passed between the detection of a previous signal and the currently detected signal. If this is the case, step 820 is carried out, where it is determined if the detection is the last detection required to validate the detection of an disquieter employing Bluetooth on this channel. If this is the case, step 822 is carried out in which the number of channels on which a Bluetooth signal is increased by one. Further, in step 824, the number of counts on the selected channel is increased. If it is determined in step 820 that the detection is not the last detection required to validate the detection of an disquieter employing Bluetooth on this channel, the method flows directly to step 824. Further, in step 826 the actual time of the global timer and the detected and signal strength is stored.

The method further proceeds with step 828, where it is decided if the current channel is the last channel which must be scanned or not. If this is the case, the method stops in step 830. If this is not the case, the method proceeds with step 832, in which a further frequency channel is selected for scanning. The method flows then back to step 802.

If in step 816, it has been determined that not enough time has been passed, the method continues with step 826. The same holds if the result of the check performed in step 814 was negative.

If in step 812, it is determined that the signal strength does not fit within the expected range, the detection continues with step 834. In step 834, it is checked, if the detected signal strength is larger that the previous detected signal strength. If this is the case, the method flows to step 836, wherein the signal strength and the global timer are stored and the previous detections made on this channel are erased. Further, in step 838, it is determined if the number of detections of the signal strength is enough in order to consider that the interfering technology was positively detected on this channel (previous to the appearance of the signal strength which was too large), the counter of the number of channels where detection is done is decreased by one in step 840. Otherwise, the detection counter is reinitialized in step 842 which also is performed subsequent to step 840. There are mainly two reasons for erasing previous detections and their consequences:

The previous detections were from another interference with lower signal strengths. Therefore, the previous detections are useless and must be erased.

The new signal strength is emitted by another interfering technology (and the previous one are due to the interfering technology sought for). This implies that there is a more harmful interfering technology that may be misleading and disturb the detections on the current channel. Thus all previous detections on this channel were probably unreliable. Therefore, the previous detections must be erased.

Subsequent to step 842, step 828 is executed as described before. If in step 834, the detected signal strength is lower than the previously detected signal strength on this channel, step 844 is performed, wherein the detected signal is discarded. Subsequently, step 828 is performed. Furthermore, if in step 810, the detected signal strength is below the threshold value, step 844 is performed as described above.

FIG. 9 shows another flow diagram illustrating steps performed by a method in accordance with the invention. The method is in particular applicable in order to detect microwaves emitted by microwave ovens via a transceiver adapted for the Zigbee standard.

In step 900, a global timer monitoring the overall scanning time is started after all variables employed have been reinitialized. In step 902, a channel of the plurality of Zigbee channels is selected. Then, in step 904, a channel timer which monitors the scanning time for the channel is started. In step 906, the channel is scanned. If during the scanning process a signal is detected, the signal strength is determined. If the actual signal strength is larger then a previously found signal strength, the actual signal strength is stored in step 908 while the previous one is discarded. In step 910, the actual scanning time monitored by the channel timer is checked against a preset maximal scanning time (tchmax). If the scanning time is smaller than the maximal scanning time, the method flows back to step 906. If the scanning time is larger than the maximal scanning time, the method proceeds with step 912.

In step 912, it is determined, if the detected signal strength matches the expected signal strength of a Microwave signal for this channel. In step 914, it is further determined if the actual scanned channel which must be scanned. If it is not the last channel, the method flows back to step 902. If in step 914, it is determined that it is the last channel, step 916 is performed, where it is decided if the number of scanned channels is sufficient in which a microwave signal has been detected (taking into account the result of step 912). If this is the case, the method proceeds with step 918, in which the number of microwave detection is increase by one. If it is not the case, the method flows back to step 902. Step 918 is followed by step 920, where it is decided if the number of microwave detections is sufficient. If this is the case, the method flow to step 922, wherein the existence of a microwave source is detected. Step 922 is then followed by step 924, wherein all variables are reinitialized. If in step 920, it has been determined that the number of detections is not sufficient, then step 926 is performed, wherein the actual global timer is compared with a specified maximal global scanning time. If the actual global timer is larger than maximal global scanning time, step 924 is performed which is followed by step 900. Otherwise, step 902 is performed.

FIG. 10 shows another flow diagram illustrating steps performed by a method in accordance with the invention. The method in accordance with the invention is in particular applicable in order to detect a disquieter employing the WiFi-standard for communication via the device with the transceiver adapted to employ the Zigbee standard.

In step 1000, all variables used within this embodiment of the method in accordance with the invention are reinitialized. In step 1002, a channel which is to be scanned is selected. In step 1004, a channel timer which monitors the scanning time for the channel is started. In step 1006, the channel is scanned. If during the scanning process a signal is detected, the signal strength is determined. If the actual signal strength is larger then a previously found signal strength, the actual signal strength is stored in step 1008 while the previous one is discarded. In step 1010, the actual scanning time monitored by the channel timer is checked against a preset maximal scanning time (tchmax). If the scanning time is smaller than the maximal scanning time, the method flows back to step 1006. If the scanning time is larger than the maximal scanning time, the method proceeds with step 1012. The signal strength detected on this channel is then stored in step 1012. In step 1014, it is decided if the scan is the last scan that must be performed. If this is not the case, the method proceeds with step 1002. If this is the case, it is determined in step 1016, if the actual scan of the channel was the last scan. If this is the case, the method proceeds with step 1018, wherein the number of scans done is increased by one. Step 1002 follows then subsequent to step 1018.

If in step 1016, it is determined that the actual scan of the channel was not the last scan, step 1020 is performed, the scans to be checked are set. In step 1022, the WiFi channels to be checked are further specified. Furthermore, in step 1024, it is determined if within all the four IEEE 802.15.4 channels (the Zigbee channels), a signal strength above a specified threshold value have been detected. If this is the case, it is furthermore determined in step 1026, if the detected signal strengths in the two mid-channels are larger than the detected signal strengths in the side channels. If this is the case, it is determined in step 1028 if the signal strength detected in the two mid-channels are sufficiently larger than the signal strengths in the two side channels. If this is the case, the number of WiFi detections on the current channels is increased by one in step 1030. In step 1032, it is determined if the number of WiFi detections on this channel is enough. If this is the case, the detection of a WiFi channel on the scanned (Zigbee) channel is detected in step 1034. In step 1036, it is determined if the actual scanned channel is the last channel to be scanned. If this is not the case, step 1022 is performed as described above. If this is the case, step 1038 is performed, where it is checked if the actual scan is the last scan. If this is not the case, step 1020 is performed, otherwise step 1000. Furthermore, if the result of any one of the checks performed in steps 1024, 1026, 1028, and 1032 is negative, step 1036 is performed subsequently.

Figure 11:
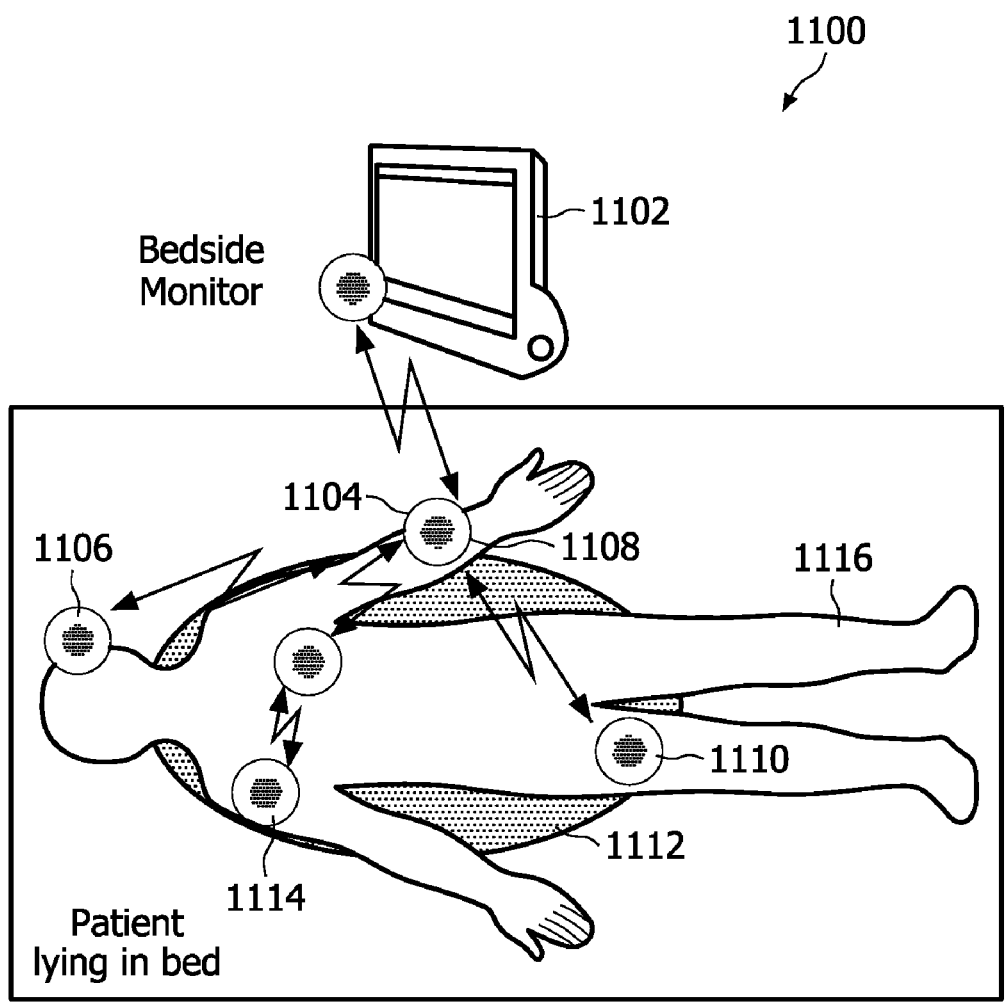
FIG. 11 shows schematically a block diagram of a body sensor network employed for monitoring a patient.

FIG. 11 shows schematically a block diagram of a wireless body sensor network 1100 employed for monitoring a patient 1116 lying in the bed. The body sensor network comprises a monitor 1102 and sensors 1104, 1106, 1108, 1110, 1112, and 1114 attached to the patient. Each sensor 1104 to 1114 might employ the methods in accordance with the invention in order to identify the interfering technology employed by one or more disquieters in the vicinity of the body sensor network. In case, a sensor detects a disquieter 1118, it might send a message to the monitor 1102 where the message is visualized. The message might contain the type of interfering technology used by the disquieter 1118 identified by the sensor. By noticing the message, the nursing stuff is able to search for the disquieter 1118 and to then remove the disquieter from the vicinity of the body sensor network.

LIST OF REFERENCE NUMERALS

100 Device
102 Disquieter
104 Microprocessor
106 IEEE 802.15.4 Card
108 Storage
110 IEEE 802.15.1 Card
112 Computer program product
114 Frequency channel
116 Frequency channel
118 Frequency channel
126 Given time window
128 Frequency channel time window
130 Signal 132 Signal strength
134 Signal
136 Signal strength
138 Signal
140 Signal strength
142 Threshold
144 Preset number of channels
146 Signal
148 Signal strength
150 Signal
152 Signal strength
154 Signal
156 Signal strength
156 Given time period
160 Measured time period
400 Graph
402 Burst
404 Burst
406 Burst
408 Abscissa
410 Ordinate
412 Duration of time
414 Time period
500 Graph
502 Abscissa
504 Ordinate
600 Spectrum
602 Abscissa
604 Ordinate
700 WLAN signal
702 Abscissa
704 Ordinate
1100 Body sensor network
1102 Monitor
1104 Sensor
1106 Sensor
1108 Sensor
1110 Sensor
1112 Sensor
1114 Sensor
1116 Patient
1118 Disquieter

The invention claimed is:

1. A method of detecting interfering technologies, the method being performed by a device, the device comprising a transceiver, the transceiver being adapted to employ a first wireless radio access technology, the method comprising:
scanning a first plurality of frequency channels provided by the first wireless radio access technology for radio signals of a first interfering technology, the first plurality of frequency channels relating to frequency channels provided by the first wireless radio access technology in which radio signals of the first interfering technology being expected;
detecting in each frequency channel of the first plurality of frequency channels the presence of a radio signal by measuring a first signal strength of the radio signal;
identifying the first interfering technology as source of the detected radio signals, if for a preset number of frequency channels of the first plurality of frequency channels the first signal strength of a radio signal is detected, or scanning a second plurality of frequency channels provided by the first wireless radio access technology for radio signals of a second interfering technology if the preset number of frequency channels will not be reached during the scanning for the first interfering technology;
determining for each frequency channel of the first plurality of frequency channels a number of detections, wherein the number of detections relates to the number of times a radio signal is detected in the corresponding frequency channel,
determining the number of frequency channels of the first plurality of frequency channels for which the number of detections exceeds an expected number of detections, wherein the expected number of detections is specified for the first interfering technology, wherein the number of frequency channels for which the number of detections exceeds the expected number of detections provides an indication for the presence of at least a second interfering technology.

2. The method according to claim 1, wherein in each frequency channel of the first plurality of frequency channels at least the first signal strength and a second signal strength are measured, wherein the second signal strength is measured for the radio signal detected subsequently to the radio signal having the first signal strength, the method further comprising:
determining a first time period relating to the time elapsed between the detection of the first signal strength and the detection of the second signal strength,
comparing the first time period with a given second time period specified for the first interfering technology, wherein the first interfering technology is identified as source of the radio signals, if for the preset number of frequency channels, the first time period determined for a frequency channel of the preset number of frequency channels at least approximately matches the second time period specified for the frequency channel.

3. The method according to claim 1, wherein the first plurality of frequency channels is scanned sequentially, wherein the first plurality of frequency channels is scanned at most for the duration of a given time window, wherein each frequency channel of the first plurality of frequency channels is scanned at most for the duration of a frequency channel scanning time window, wherein the scanning time for identifying the first interfering technology is compared with a minimum required scanning time, wherein the minimum required scanning time is specified for the first interfering technology, wherein the first interfering technology is identified as not being the source of the radio signals if the actual scanning time is below the minimum required scanning time.

4. The method according to claim 1, wherein the first plurality of frequency channels is scanned sequentially, wherein each frequency channel of the first plurality of frequency channels is scanned until a preset number of radio signals are detected, wherein the scanning time for detecting the preset number of radio signals is compared with a minimum required scanning time, wherein the minimum required scanning time is specified for the first interfering technology, wherein the first interfering technology is identified as not being the source of the radio signals detected in the channel, if the actual scanning time is below the minimum required scanning time.

5. The method according to claim 1, wherein the first plurality of frequency channels in which it is scanned for radio signals is selected according to characteristics of the first interfering technology, wherein the second interfering technology is selected according to properties of the radio signals detected during the scan for the first interfering technology, wherein the at least first signal strengths measured during the scan for the first interfering technology are employed for the identification of the second interfering technology.

6. The method according to claim 1, wherein a first spectrum shape specifies for the first plurality of frequency channels expected relative signal strengths for the first interfering technology, wherein the at least first signal strengths measured in frequency channels of the first plurality of frequency are employed to determine relative first signal strengths for the frequency channels, wherein the first interfering technology is identified as source of the detected radio signals, if the relative first signal strengths determined for the frequency channels in which the at least first signal strengths have been detected match the expected relative signal strengths specified for the frequency channels.

7. The method according to claim 6, wherein the first signal strength is measured in a first frequency channel of the first plurality of frequency channels, wherein a third signal strength is measured in a second frequency channel of the first plurality of frequency channels, wherein a first ratio is determined between the first signal strength and the third signal strength, wherein a second ratio is determined between the expected signal strengths specified by the first spectrum shape for the first and second frequency channels, wherein the first and the second ratio are compared, wherein the first interfering technology is not considered as source if the first ratio does not at least approximately match the second ratio.

8. The method according to claim 7, wherein a second spectrum shape is specified for the second interfering technology, wherein a third ratio is determined between the expected signal strengths specified by the second spectrum shape for the first and second frequency channels, wherein it is further scanned for the second interfering technology if the first ratio does at least approximately match the third ratio.

9. The method according to claim 1, further comprising:
measuring a pulse length for detected radio signals, wherein the pulse length of a radio signal relates to the period of time during which the signal strength of the radio signal is above the threshold value,
comparing the measured pulse lengths of the detected radio signals with an expected pulse length for the first interfering technology, wherein the first interfering technology is identified as source of some of the detected radio signals, if at least some of the measured pulse lengths match the expected pulse length.

10. The method according to claim 9, wherein the measured pulse lengths which do not match the expected pulse length specified for the first interfering technology are compared with expected pulse lengths specified for the second interfering technology, wherein the second interfering technology is identified as source of some of the detected radio signals, if at least some of the measured pulse lengths match the expected pulse length specified for the second interfering technology.

11. The method according to claim 1, wherein in each frequency channel of the first plurality of frequency channels at least the first signal strength and a second signal strength are measured, wherein the second signal strength is measured for the radio signal detected subsequently to the radio signal having the first signal strength, wherein the second signal strength is only taken into account for identifying the first interfering technology if the magnitude of the first signal strength at least approximately matches the magnitude of the second signal strength.

12. A computer program product comprising a non-transitory computer-readable medium that stores computer executable instructions, the instructions being adapted to perform the method according to claim 1.

13. A device comprising:
a transceiver, wherein the transceiver is adapted to employ a first wireless radio access technology,
means for scanning a first plurality of frequency channels provided by the first wireless radio access technology for radio signals of a first interfering technology, the first plurality of frequency channels relating to frequency channels provided by the first wireless radio access technology in which radio signals of the first interfering technology being expected;
means for detecting in each frequency channel of the first plurality of frequency channels the presence of a radio signal by measuring a first signal strength of the radio signal;
means for identifying the first interfering technology as source of the detected radio signals, if for a preset number of frequency channels of the first plurality of frequency channels the first signal strength of a radio signal is detected, or scanning a second plurality of frequency channels provided by the first wireless radio access technology for radio signals of a second interfering technology if the preset number of frequency channels will not be reached during the scanning for the first interfering technology;
means for determining for each frequency channel of the first plurality of frequency channels a number of detections, wherein the number of detections relates to the number of times a radio signal is detected in the corresponding frequency channel; and
means for determining the number of frequency channels of the first plurality of frequency channels for which the number of detections exceeds an expected number of detections, wherein the expected number of detections is specified for the first interfering technology, wherein the number of frequency channels for which the number of detections exceeds the expected number of detections provides an indication for the presence of at least a second interfering technology.

14. The device according to claim 13, further comprising:
means for measuring at least the first signal strength and a second signal strength, wherein the second signal strength is measured for the radio signal detected subsequently to the radio signal having the first signal strength,
means for determining a first time period relating to the time elapsed between the detection of the first signal strength and the detection of the second signal strength,
means for comparing the first time period with a given second time period specified for the first interfering technology, wherein the first interfering technology is identified as source of the radio signals, if for the preset number of frequency channels, the first time period determined for a frequency channel of the preset number of frequency channels at least approximately matches the second time period specified for the frequency channel.

15. A sensor comprising the device according to claim 13.

16. A patient monitor comprising the device according to claim 13.

17. A body sensor network comprising one or more sensors according to claim 15 and one or more patient monitors.

* * * * *